(12) United States Patent
Ba-Abbad

(10) Patent No.: US 8,883,484 B2
(45) Date of Patent: Nov. 11, 2014

(54) METHOD AND SYSTEM FOR PROCESSING ORGANIC MATTER IN A POULTRY FARM

(75) Inventor: Mazen A. Ba-Abbad, Riyadh (SA)

(73) Assignee: King Abdulaziz City for Science and Technology (KACST), Riyadh (SA)

( * ) Notice: Subject to any disclaimer, the term of this patent is extended or adjusted under 35 U.S.C. 154(b) by 1031 days.

(21) Appl. No.: 12/763,817

(22) Filed: Apr. 20, 2010

(65) Prior Publication Data

US 2011/0256614 A1 Oct. 20, 2011

(51) Int. Cl.
| | |
|---|---|
| *C02F 3/34* | (2006.01) |
| *A62D 3/00* | (2006.01) |
| *A62D 3/02* | (2007.01) |
| *B09B 3/00* | (2006.01) |
| *B09C 1/10* | (2006.01) |
| *C12M 1/00* | (2006.01) |
| *C12M 3/00* | (2006.01) |
| *A01K 31/04* | (2006.01) |
| *A01K 1/01* | (2006.01) |

(52) U.S. Cl.
CPC .................. *B09B 3/00* (2013.01); *C12M 43/00* (2013.01); *B09B 3/0083* (2013.01); *A01K 31/04* (2013.01); *A01K 1/01* (2013.01); *C12M 21/02* (2013.01)

USPC .................... 435/262.5; 435/262; 435/283.1; 435/289.1; 435/290.1

(58) Field of Classification Search
USPC .......................... 435/262.5, 283.1–309.4, 262
See application file for complete search history.

(56) References Cited

U.S. PATENT DOCUMENTS

| | | | | |
|---|---|---|---|---|
| 5,772,721 | A * | 6/1998 | Kazemzadeh | .................... 71/11 |
| 6,416,993 | B1 * | 7/2002 | Wexler et al. | ............... 435/262.5 |
| 6,896,804 | B2 * | 5/2005 | Haerther et al. | ............... 210/602 |
| 2008/0050800 | A1 * | 2/2008 | McKeeman et al. | ........ 435/262.5 |
| 2010/0105127 | A1 * | 4/2010 | Ginsburg | ...................... 435/262 |

* cited by examiner

Primary Examiner — Nathan Bowers
Assistant Examiner — Lydia Edwards
(74) Attorney, Agent, or Firm — Timberline Patent Law Group PLLC

(57) ABSTRACT

The invention provides a method and system for processing organic matter that is produced in a poultry farm. The organic matter produced by the plurality of birds is removed from one or more containers that house the plurality of birds. The method further includes treating a first amount of organic matter of the organic matter in a thermal processor to produce inorganic matter. Thereafter, the inorganic matter and a second amount of organic matter of the organic matter are consumed in one or more photo bioreactors for growing one or more photosynthesis organisms.

17 Claims, 7 Drawing Sheets

METHOD AND SYSTEM FOR PROCESSING ORGANIC MATTER IN A POULTRY FARM

FIELD OF THE INVENTION

The present invention generally relates to processing of organic matter in a poultry, and more specifically, to a method and system for efficiently removing the organic matter from a poultry farm and consuming the organic matter using one or more photo bioreactors in a poultry farm.

BACKGROUND OF THE INVENTION

Poultry farm operations produce a significant amount of waste material, exhale gases and odor that contaminates the environment. As a result, poultry farms are usually located far from residential areas at remote locations. Examples of such waste material include, but are not limited to, organic matter, slaughter remains, ammonia, sulfur dioxide, nitrogen, and methane that is produced due to the slaughter remains and exhale gases of farm animals. The waste material, exhale gases and odor produced from poultry farms may spread through air, water or by farm animals and farm workers. The waste material and the odor, if not managed properly, pose a serious health risk to the farm animals and human beings present in the vicinity of the poultry farms.

Farm animals such as chickens, turkeys, geese, and ducks are kept in close vicinity to each other in the poultry farms and are not properly isolated. Such high density living conditions can transmit diseases inside the poultry farms and result in a disease outbreak. If the poultry farms are not properly isolated, then the disease may spread to human beings through air and water.

In order to reduce environmental hazards caused due to production of odor from poultry waste material, air conditioning is used inside the poultry farms. Further, open air circulation and water spray cooling systems are also utilized for controlling odor produced in the poultry farms. However, this requires a huge amount of water and also water is not easily available and in abundance at all the places. Further, the amount of power that is required to run the air conditioning units is large and expensive.

Notwithstanding the problems and detrimental effects mentioned above, proper treatment of organic matter produced from poultry farms can act as a good nutritional source for photosynthesis organism such as algae. However, the existing technologies do not make use of the organic matter to convert the organic matter into a nutritional source for plants while effectively reducing the problems caused due to the organic matter in the poultry farms Therefore, there is a need for a method and an integrated system to provide a closed and an isolated environment for farm animals while efficiently processing the waste material and odor that is produced and reduce the cost of maintaining the poultry farms.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the invention.

Figure 1:
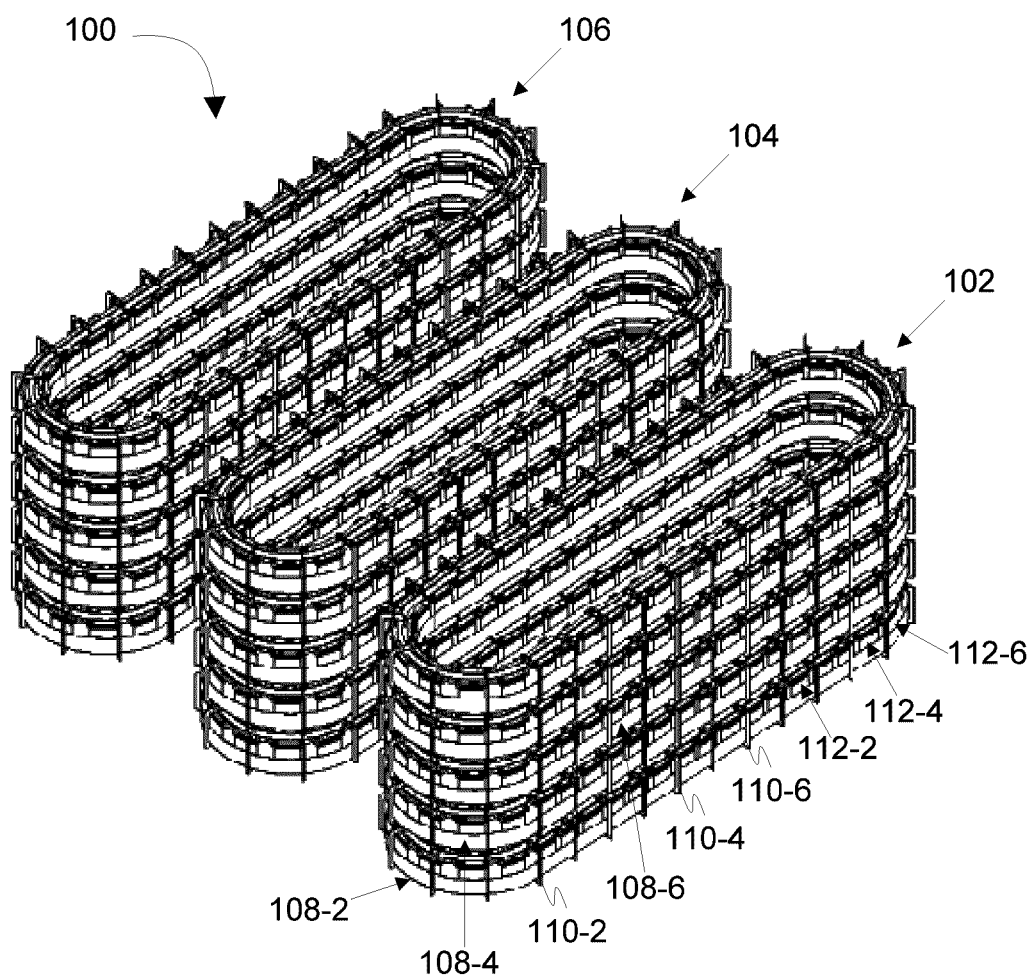
FIG. 1 illustrates a poultry farm for housing a plurality of birds in accordance with an embodiment of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION OF THE INVENTION

Before describing in detail embodiments that are in accordance with the invention, it should be observed that the embodiments reside primarily in combinations of method steps and apparatus components related to method and system for processing organic material produced in a poultry farm. Accordingly, the apparatus components and method steps have been represented where appropriate by conventional symbols in the drawings, showing only those specific details that are pertinent to understanding the embodiments of the invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Various embodiments of the invention provide methods and system for processing organic matter produced in a poultry farm. A method includes removing organic matter obtained from a plurality of birds and thermally treating a first amount of organic matter of the organic matter in a thermal processor to produce inorganic matter. The method further includes utilizing the inorganic matter and a second amount of organic matter of the organic matter for growing photosynthesis organism such as algae in one or more photo bioreactors.

FIG. 1 illustrates a poultry farm 100 for housing a plurality of birds in accordance with an embodiment of the invention.

Poultry farm 100 includes one or more housing units such as a housing unit 102, a housing unit 104 and a housing unit 106 which are arranged horizontally inside the poultry farm. In an embodiment, the one or more housing units may be arranged vertically or randomly positioned inside the poultry farm. Each housing unit of the one or more housing units includes one or more rails such as a rail 108-2, a rail 108-4, and a rail 108-6 and so on. The one or more rails are fixed and held in a position using one or more rail holders such as a rail holder 110-2, a rail holder 110-4 and a rail holder 110-6 and so on. The one or more rails may be configured to move in a linear or a curvilinear motion such that any object that is mounted on the one or more rails traverses a distance covered by the one or more rails.

The one or more rails are arranged vertically inside the one or more housing units and have a plurality of containers mounted on them. For example, a container 112-2, a container 112-4, and a container 112-6 and so on are mounted on rail 108-2. This is further explained in detail in conjunction with FIG. 2. A container of the plurality of containers houses one or more birds of the plurality of birds. Examples of birds may include, but are not limited to, chicken, turkey, duck, and geese. The volume of each container of the plurality of containers is large enough to provide enough space for accommodating the one or more birds. Further, height of each container of the plurality of containers ensures that the one or more birds are not exposed to any kind of contamination. In an embodiment, the plurality of containers may be moved from one place to another on the one or more rails using a locomotive (not shown in FIG. 1). In another embodiment, a container of the plurality of containers may be a hanging fixed cage that may be moved for maintenance and servicing from one place to another on the one or more rails.

Each container of the plurality of containers may be removed from the one or more rails for servicing. For example, container 112-2 may be removed from rail 108-2 for maintenance and servicing. In order to remove the containers for maintenance and servicing, a chicken service vehicle (not shown in FIG. 1) may be used. The chicken service vehicle may also be utilized for cleaning the plurality of containers, providing feed to the one or more birds, and for moving the one or more birds from housing unit to another housing unit or for moving the one or more birds from one rail of the one or more rails to another rail of the one or more rails. The arrangement of the one or more housing units horizontally saves floor space of the poultry farm. Further, the arrangement of the one or more rails inside the one or more housing units also saves floor space of the poultry farm and allows for handling of the one or more birds in an easy and efficient manner. For example, in case of a disease breakout in the poultry farm, one or more of the plurality of containers may be isolated for facilitating easy cleaning of the one or more of the plurality of containers and for treatment of the one or more birds.

Figure 2:
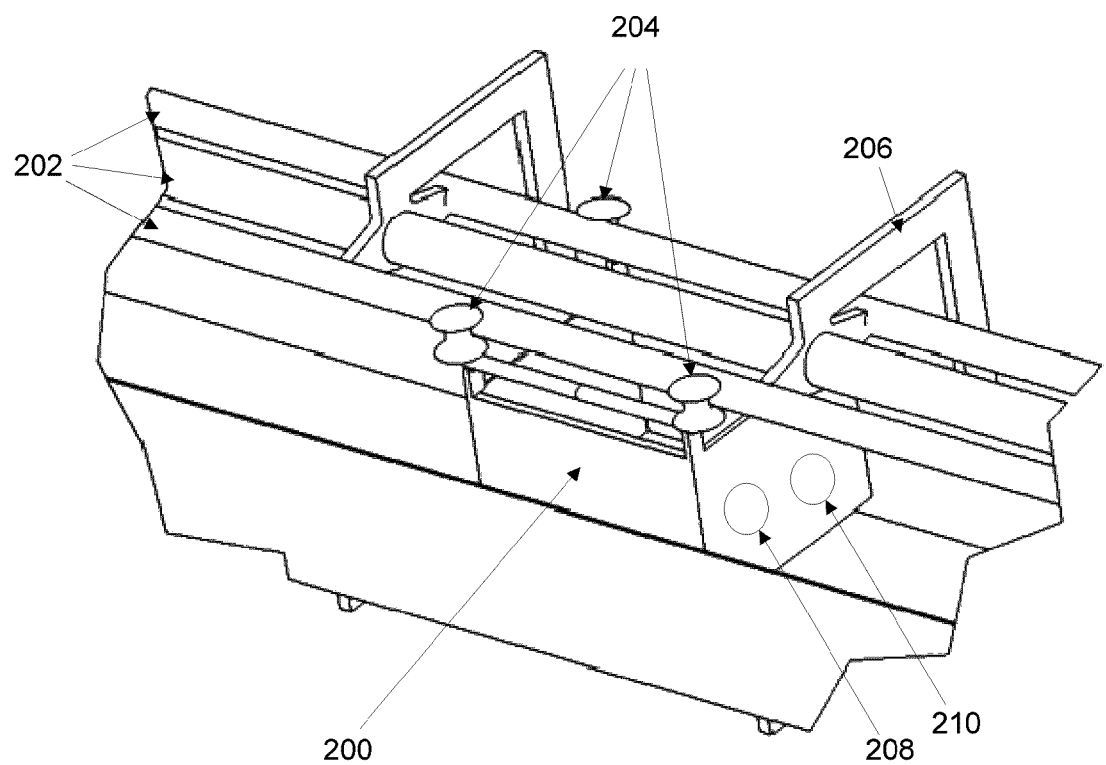
FIG. 2 illustrates a container of the plurality of containers for collecting organic matter obtained from one or more birds of the plurality of birds in accordance with an embodiment of the invention.

FIG. 2 illustrates a container 200 of the plurality of containers for collecting organic matter obtained from one or more birds of the plurality of birds in accordance with an embodiment of the invention. Container 200 houses one or more birds of the plurality of birds inside it. Organic matter that is obtained from the one or more birds housed in container 200 is collected inside container 200. Examples of the organic matter may include, but is not limited to excreta, blood, bones, hair, ammonia, nitric oxide, slaughter remains, and organs. In order to remove the organic matter, container 200 is provided with a first opening 208 and a second opening 210. In an embodiment, a first amount of organic matter of the organic matter obtained from the one or more birds of the plurality of birds may be removed from container 200 using first opening 208. In the same manner, a second amount of organic matter of the organic matter may be removed from container 200 using second opening 210.

First opening 208 and second opening 210 may also be utilized for removing exhale gases produced by the one or more birds from container 200. For example, carbon dioxide and methane that is present in exhale gases produced by the one or more birds may be removed from container 200 using first opening 208 and second opening 210. Further, gases produced due to biological decay of the organic matter obtained from the one or more birds may also be removed using first opening 208 and second opening 210. For example, methane that is produced due to biological decay of the organic matter obtained from the one or more birds may be removed using first opening 208 and second opening 210. It will be appreciated by a person skilled in the art that container 200 may have any number of openings for removing the one or more of the organic matter and the exhale gases from container 200 and the one or more openings may be used in any number of combinations to remove the one or more of the organic matter and the exhale gases. This is further explained in detail in conjunction with FIG. 3.

As explained in FIG. 1, container 200 is moveably coupled to one or more rails such that container 200 traverses a distance covered by the one or more rails. Container 200 may be moveably coupled to the one or more rails using one or more of wheels, balls, a shaft and any other mechanical means required for coupling container 200 to the one or more rails. For example, as shown in FIG. 2, container 200 is moveably coupled to a rail 202 using wheels 204. Rail 202 is fixed and held in position using a rail holder 206. In an embodiment, container 200 may be fixed to the one or more rails. In another embodiment, container 200 may be electro-magnetically coupled to the one or more rails.

Figure 3:
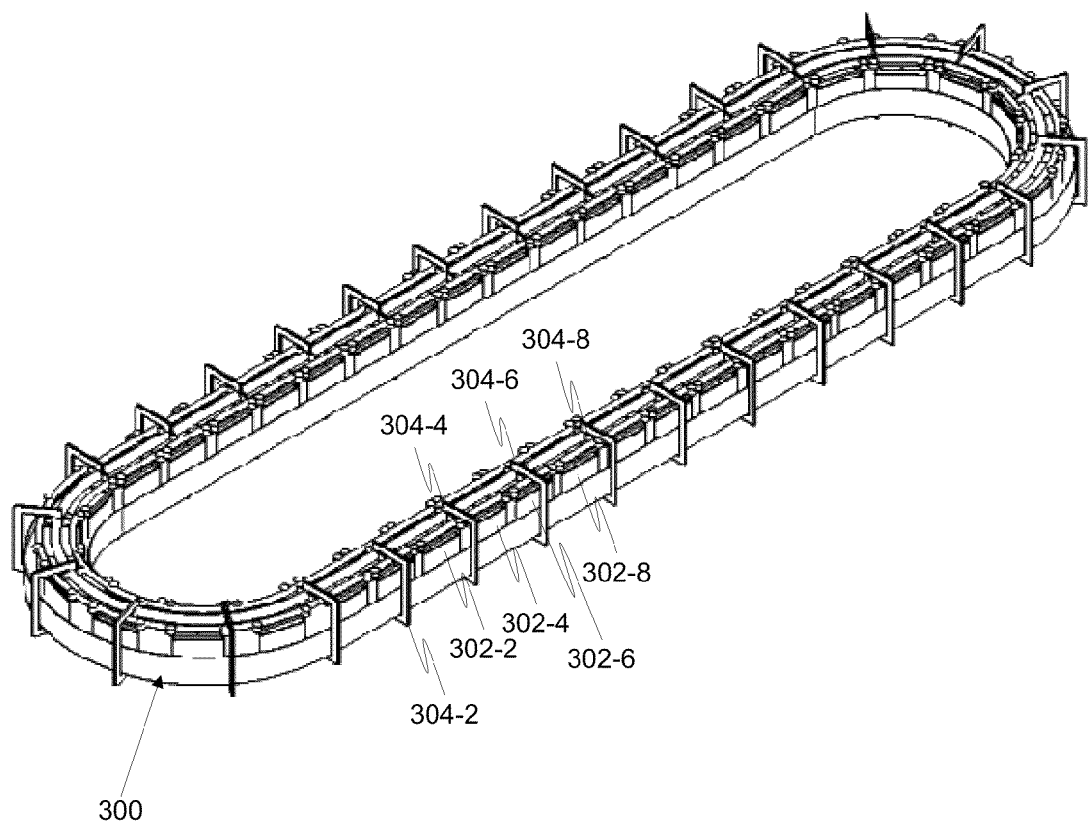
FIG. 3 illustrates a rail of the one or more rails in accordance with an embodiment of the invention.

FIG. 3 illustrates a rail 300 of the one or more rails in accordance with an embodiment of the invention. One or more containers of the plurality of containers such as a container 302-2, a container 302-4, a container 302-6 and a container 302-8, and so on are moveably coupled to rail 300. In an embodiment, rail 300 is fixed and held in a position using one or more rail holders such as a rail holder 304-2, a rail holder 304-4, a rail holder 304-6, and a rail holder 304-8 and so on. Further, the one or more containers of the plurality of containers may be interconnected such that the one or more containers move together and traverse a distance covered by the one or more rails. For example, as shown in FIG. 3, container 302-2, container 302-4, container 302-6, and container 302-8 are interconnected and move like a rollercoaster on rail 300. In another embodiment, container 302-2, container 302-4, container 302-6, and container 302-8 may be isolated from each other and move independently.

As explained in FIG. 2, each container of the plurality of containers has a first opening and a second opening for removing organic matter produced by one or more birds of the plurality of birds. In an embodiment, the organic matter may be removed from the plurality of containers using a vacuum pump. The one or more containers are further connected to a thermal processor (not shown in FIG. 3). The thermal processor receives a first amount of organic matter of the organic matter produced by the one or more birds. In response to receiving the first amount of organic matter, the thermal processor thermally treats the first amount of organic matter to produce inorganic matter. Examples of inorganic matter may include, but are not limited to one or more gases, and inorganic ash. The one or more gases may include, but are not limited to, nitrogen, carbon dioxide, and sulfur dioxide. Methane may also be produced in the thermal processor if the organic matter is incompletely burnt in the thermal processor. Accordingly, the thermal processor may convert methane thus produced into carbon dioxide. In an embodiment, the thermal processor is located at remote location from the one or more containers. For example, the thermal processor may be located outside a poultry farm. This is done to ensure that the one or more birds do not come in contact with the inorganic matter produced in thermal processor. Thus, health and safety of the one or more birds is maintained by ensuring that the one or more birds are not exposed to the thermal processor.

The thermal processor is further connected to an exhaust unit (not shown in FIG. 3) for removing the one or more gases that are produced in the thermal processor. For example, ammonia may be removed from the thermal processor through the exhaust unit. This ensures that poisonous gases such as ammonia are removed from the thermal processor and the one or more birds are not exposed to the poisonous gases.

In an embodiment, the exhaust unit removes the one or more gases produced in the thermal processor. The one or more gases such as carbon dioxide removed by the exhaust unit may be utilized for feeding one or more photosynthesis organisms. This is further explained in detail in FIG. 4.

In an embodiment, the exhaust unit may remove the organic matter from the one or more containers of the plurality of containers. This facilitates in providing hygienic conditions for the one or more birds present in the one or more containers. Further, as the organic matter is removed from the one or more containers by the exhaust unit, the one or more birds are not exposed to any kind of contamination that may arise due to presence of the organic matter in the one or more containers. In an embodiment, the exhaust unit may also be configured to remove exhale gases from the one or more birds present in the one or more containers so as to maintain exhale gases free environment around the one or birds.

Figure 4:
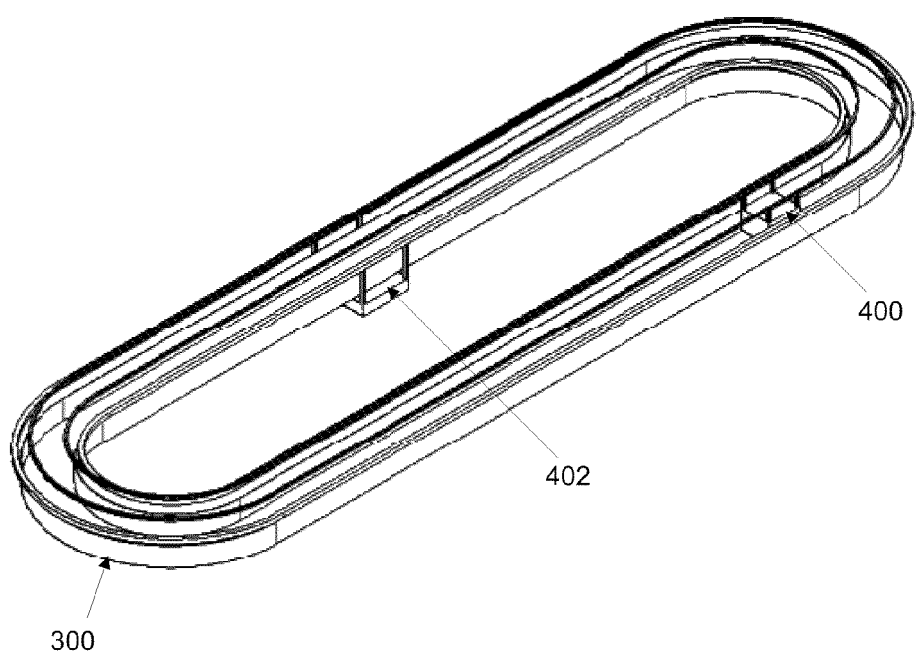
FIG. 4 illustrates an inner view of a rail showing an organic matter removal mechanism for removing the organic matter from the one or more containers in accordance with an embodiment of the invention.

FIG. 4 illustrates an inner view of rail 300 showing an organic matter removal mechanism for removing the organic matter from the one or more containers in accordance with an embodiment of the invention. Container 400 houses one or more birds of the plurality of birds and has a first opening and a second opening for removing organic matter produced by the one or more birds. A first amount of organic matter of the organic matter is supplied to the thermal processor using the first opening to produce inorganic matter. This has already been explained in FIG. 3.

Further, a second amount of organic matter of the organic matter is collected from the second opening. Thereafter, the inorganic matter and the second amount of organic matter are supplied to one or more photo bioreactors for facilitating growth of one or more photosynthesis organisms in the one or more photo bioreactors. The one or more photo bioreactors may be one or more of a race-way type photo bioreactor with a steering pedal, a flat plate-type photo bioreactor, and a tubular type photo bioreactor. Further, the one or more photo bioreactors are isolated from outside air.

In an embodiment, the second amount of organic matter is delivered to the one or more photo bioreactors using one or more service vehicles such as a service vehicle 402 as shown in FIG. 4. In an embodiment, the second amount of organic matter of the organic matter may be directly supplied from the one or more containers of the plurality of containers to the one or more photo bioreactors. Similarly, the one or more photo bioreactors receive the inorganic matter produce by the thermal processor. In an embodiment, service vehicle 402 may be configured to receive the inorganic matter produced by the thermal processor and deliver the inorganic matter to the one or more photo bioreactors.

The second amount of organic matter of the organic matter and the inorganic matter is consumed by the one or more photo bioreactors for growing the one or more photosynthesis organisms. For example, the one or more photo bioreactors may consume the second amount of organic matter and the inorganic matter for growing algae. In an embodiment, the second amount of organic matter and the inorganic matter may be mixed before supplying to the one or more photo bioreactors. In another embodiment, only one of the second amount of organic matter of the organic matter and the inorganic matter may be consumed by the one or more photo bioreactors.

The consumption of the second amount of organic matter of the organic matter and the inorganic matter by the one or more photosynthesis organisms facilitate in reducing odor. For example, the one or more photosynthesis organisms may absorb ammonia, nitric oxide, and the one or more gases such as carbon dioxide to reduce odor.

Further, since the one or more photosynthesis organisms consume carbon dioxide and produce oxygen, the one or more photosynthesis organisms may be utilized as a source of oxygen to the one or more birds in the poultry farm. This facilitates in isolating the poultry farm from outside environment and avoiding any requirement of utilizing an external vent for supplying fresh oxygen to the one or more birds.

In order to facilitate the growth of the one or more photosynthesis organisms, the one or more photo bioreactors are coupled with a light source. The light source supplies light energy to the one or more photo bioreactors. Examples of the light source may include bulb, incandescent lamps, and electric lamps. In an embodiment, sunlight may be supplied to the one or more photo bioreactors as a source of light energy. Further, a water source may be used for supplying water to the one or more photo bioreactors for facilitating the growth of the one or more photosynthesis organisms.

Additionally, a temperature controller may also be utilized to control temperature of the one or more photo bioreactors. Examples of the temperature controller may include an air conditioning unit, a fan, and a water cooling & heating unit. In an embodiment, the temperature controller such a water cooling & heating unit may be used to control temperature of water present in the one or more photo bioreactors. The temperature of water can in turn govern the air temperature in the poultry farm. Further, as water has heat capacity larger than air and as the poultry farm is isolated from the outside environment, the cost of maintaining the air temperature of the poultry farm is reduced. This facilitates in saving electric energy that is required to run the temperature controller.

The temperature controller may also be configured to control temperature of the one or more containers based on a policy. The one or more birds need a certain temperature for their growth at different stages of their life. Accordingly, the policy may contain information about a required temperature corresponding to different stages of the one or more birds' lives. The policy may be fed to a logical unit associated with the temperature controller. As a result, the temperature controller controls the temperature in the one or more containers based on the information present in the policy.

The one or more photo bioreactors may also be adaptively coupled to an air unit. The air unit may be configured to supply air through the water in the one or more photo bioreactors. This facilitates in the growth of the one or more photosynthesis organisms. Additionally, an exhaust unit may be used for removing exhale gases from the one or more birds present in the one or more containers and deliver the exhale gases to the one or more photo bioreactors. For example, the exhaust unit may supply carbon dioxide exhaled by the one or more birds to the one or more photo bioreactors to facilitate the growth of the one or more photosynthesis organism. This has already been explained in FIG. 3.

Figure 5:
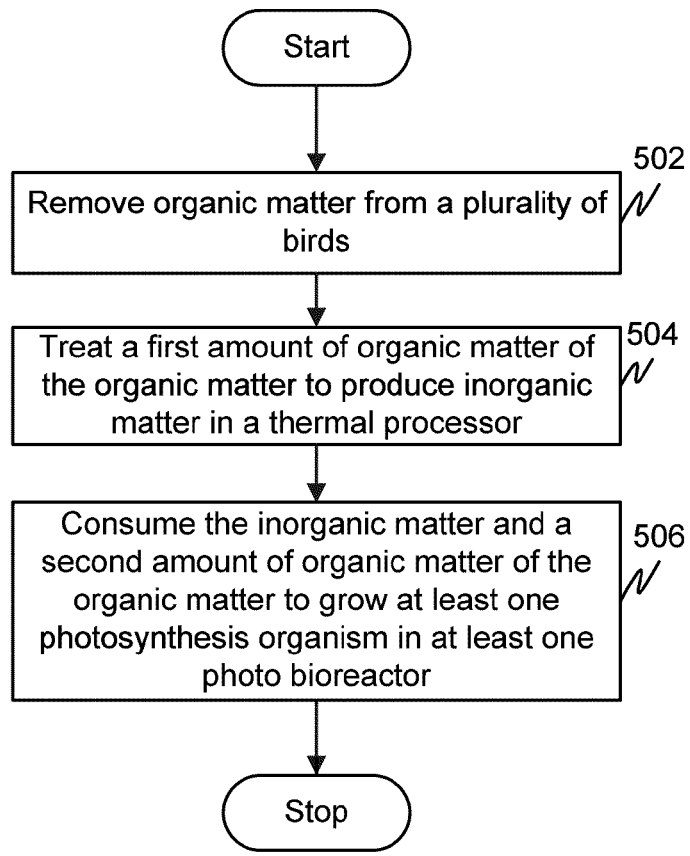
FIG. 5 is a flowchart of a method for processing organic matter in a poultry farm in accordance with an embodiment of the invention.

FIG. 5 is a flowchart of a method for processing organic matter in a poultry farm in accordance with an embodiment of the invention. The poultry farm houses a plurality of birds in a plurality of containers. At step 502, the organic matter produced by one or more birds of the plurality of birds in one or more containers of the plurality of containers is removed using a first opening and a second opening associated with each container of the one or more containers. This has already been explained in FIG. 2. After removing the organic matter from the one or more containers, at step 504, a first amount of organic matter of the organic matter is thermally treated in a thermal processor to produce inorganic matter. This has already been explained in FIG. 3. The inorganic matter may include, but is not limited to, one or more gases and an inorganic ash. Example of the one or more gases may include, but is not limited to methane, sulfur dioxide and nitrogen. This is further explained in conjunction with FIG. 6.

The inorganic matter produced in the thermal processor is sent to one or more photo bioreactors. Thereafter, at step 506, the inorganic matter is consumed along with a second amount of organic matter of the organic matter in the one or more photo bioreactors for growing one or more photosynthesis organisms. For example, the inorganic and the second amount of organic matter of the organic matter may be consumed in the one or more photo bioreactors to grow algae. This is further explained in conjunction with FIG. 7.

Figure 6:
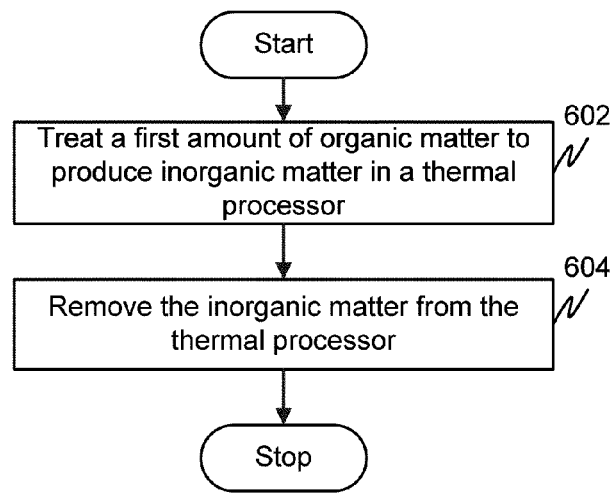
FIG. 6 is a flowchart of a method for removing inorganic matter from the thermal processor in accordance with an embodiment of the invention.

FIG. 6 is a flowchart of a method for removing inorganic matter from the thermal processor in accordance with an embodiment of the invention. The thermal processor receives a first amount of organic matter of the organic matter. At step 602, the thermal processor thermally treats the first amount of organic matter of the organic matter to produce the inorganic matter. The inorganic matter may include, but is not limited to, one or more gases and an inorganic ash. This has already been explained in FIG. 5. After producing the inorganic matter, at step 604, the exhaust unit removes the one or more gases from the thermal processor. The exhaust unit may remove the one or more gases and store the removed gases in a storage unit. This facilitates easy collection of the one or more gases for further processing. For example, methane removed from the thermal processor may be stored by the exhaust unit in the storage unit for processing. In an embodiment, the exhaust unit may remove the one or more gases for separating the poisonous and toxic components present in the one or more gases.

Figure 7:
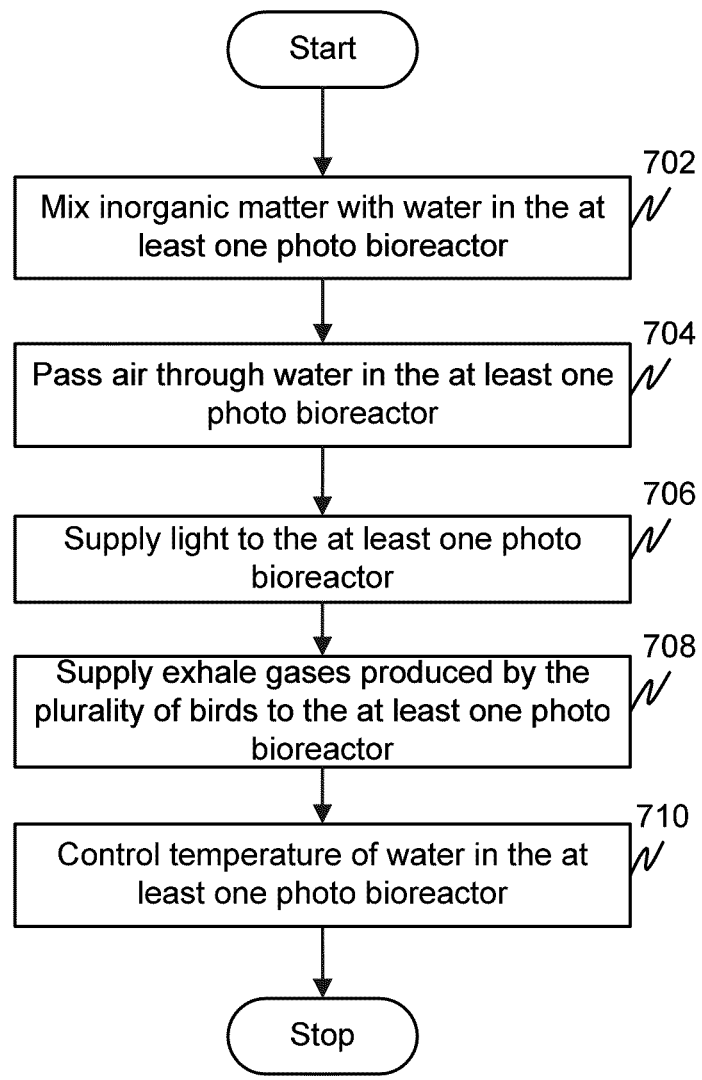
FIG. 7 is a flowchart of a method for consuming inorganic matter and organic matter in one or more photo bioreactors in accordance with an embodiment of the invention.

FIG. 7 is a flowchart of a method for consuming inorganic matter and organic matter in one or more photo bioreactors in accordance with an embodiment of the invention. The one or more photo bioreactors receive the inorganic matter produced by the thermal processor and a second amount of organic matter of the organic matter from the one or more containers of the plurality of containers. In an embodiment, the inorganic matter and the second amount of organic matter may be mixed before supplying to the one or more photo bioreactors. In another embodiment, only one of the second amount of organic matter and the inorganic matter may be consumed by the one or more photo bioreactors. At step 702, the inorganic matter is mixed with water in the one or more photo bioreactors. Thereafter, at step 704, air is passed through water that is present in the one or more photo bioreactors. In an embodiment, air may be passed through water before mixing the inorganic matter with water in the photo bioreactors. After passing air through water present in the one or more photo bioreactors, light energy is supplied to the one or more photo bioreactors. The light energy may be supplied using a light source. Examples of light source may include, but are not limited to a bulb, incandescent lamps, and electric lamps. In an embodiment, direct sunlight may be allowed to fall on the one or more photo bioreactors. Further, light energy may be continuously supplied even before the inorganic matter is supplied to the one or more photo bioreactors.

At step 708, the exhaust unit supplies exhale gases produced by one or more birds of the plurality of birds to the one or more photo bioreactors. For example, the exhaust unit may supply carbon dioxide that is produced by the one or more birds of the plurality of birds to the one or more photo bioreactors. Subsequently, at step 710, a temperature controller is utilized for controlling temperature of the one or more photo bioreactors. Examples of the temperature controller may include, but are not limited to an air-conditioning unit, a fan, a cooler, and a water cooling & heating unit. The temperature controller may be used for controlling temperature of water that is present in the one or more photo bioreactors. Further, a logical unit present in the temperature controller may be configured to dynamically change the temperature of the one or more photo bioreactors based on a policy. The policy contains information about a required temperature corresponding to different stages of the one or more birds' lives. The policy is fed to the logical unit and based on the various stages and the required temperature value corresponding to the various stages of the one or more bird's lives defined in the policy, the logical unit may dynamically change the temperature of the one or more photo bioreactors. This has already been explained in FIG. 4.

Various embodiments of the invention provide methods and systems for processing organic matter that is produced in a poultry farm housing a plurality of birds. The system removes the organic matter in an efficient manner and provides a clean and hygienic environment for the plurality of birds that are housed in the poultry farm and eliminates environmental contamination caused due to the poultry farm. Further, the system reduces the problem of odor that is produced in the poultry farm. The method and system also reduce the cost of air-conditioning that is required for the poultry farm. Still further, the method and system produce valuable nutrients that facilitate in the growth of one or more photosynthesis organisms by converting the organic matter to inorganic matter.

Those skilled in the art will realize that the above recognized advantages and other advantages described herein are merely exemplary and are not meant to be a complete rendering of all of the advantages of the various embodiments of the present invention.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of the present invention. The benefits, advantages, solutions to problems, and any element(s) that may cause any benefit, advantage, or solution to occur or become more pronounced are not to be construed as a critical, required, or essential features or elements of any or all the claims. The present invention is defined solely by the appended claims including any amendments made during the pendency of this application and all equivalents of those claims as issued.

What is claimed is:

1. A system for processing organic matter in a poultry farm, the poultry farm comprising a plurality of birds, the system comprising:
   a plurality of containers, wherein each container houses at least one bird, the container having a first opening and a second opening for removing the organic matter obtained from the at least one bird;
   a thermal processor adaptively connected to each container for receiving a first amount of the organic matter; wherein the first amount of the organic matter is thermally treated in the thermal processor for converting the organic matter to inorganic matter; and
   at least one photo bioreactor adaptively connected to each container and the thermal processor, wherein the at least one photo bioreactor houses at least one photosynthesis organism, wherein the at least one photo bioreactor is configured to:
      receive a second amount of the organic matter associated with each container and the inorganic matter from the thermal processor; and
      consume the second amount of organic matter and the inorganic matter for converting carbon dioxide to oxygen in the at least one photo bioreactor.

2. The system of claim 1, wherein the system further comprises at least one rail, wherein the at least one rail is held by at least one rail holder.

3. The system of claim 2, wherein each container of the plurality of containers comprises at least one wheel, wherein the at least one wheel is moveably coupled to the at least one rail.

4. The system of claim 2, wherein a rail of the at least one rail is a fixed race-way type rail.

5. The system of claim 1, wherein the thermal processor is located at a remote location from the plurality of containers.

6. The system of claim 1, wherein the at least one photo bioreactor is one of a race-way type photo-bioreactor with a steering pedal, a flat plate-type photo bioreactor, and a tubular-type photo bioreactor.

7. The system of claim 1 further comprising a light source, wherein the light source is configured to provide light to the at least one photo bioreactor.

8. The system of claim 1 further comprising a temperature controller, wherein the temperature controller is configured to control the temperature of water in the at least one photo bioreactor based on a policy, wherein the policy defines a required range of temperature for each stage of a bird's life.

9. The system of claim 1 further comprising an exhaust unit, wherein the exhaust unit is configured to remove the organic matter from the plurality of containers and the inorganic matter from the thermal processor.

10. The system of claim 9, wherein the exhaust unit is further configured to deliver exhale gases from the plurality of containers to the at least one photo bioreactor, wherein the exhale gases are produced from the plurality of birds.

11. A method of processing organic matter in a poultry farm isolated from an outside environment, the poultry farm comprising a plurality of birds, the method comprising:
   removing the organic matter from at least one bird of the plurality of birds;
   treating a first amount of the organic matter with a thermal processor to convert the organic matter to inorganic matter, the inorganic matter including carbon dioxide; and
   consuming in at least one photo bioreactor of the inorganic matter and a second amount of the organic matter for growing at least one photosynthesis organism in the at least one photo bioreactor to convert the carbon dioxide to oxygen within the poultry farm isolated from the outside environment.

12. The method of claim 11, wherein the organic matter obtained from the plurality of birds comprises at least one of excreta, blood, bones, hair, ammonia, and organs.

13. A method of processing organic matter in a poultry farm, the poultry farm comprising a plurality of birds, the method comprising:
   processing each container in turn of a sequence of containers moving in an endless loop on a rail;
   removing the organic matter from at least one bird;
   treating a first amount of the organic matter with a thermal processor to convert the organic matter to inorganic matter;
   consuming the inorganic matter and a second amount of the organic matter for growing at least one photosynthesis organism in at least one photo bioreactor to convert carbon dioxide to oxygen;
   wherein consuming comprises mixing the inorganic matter with the second amount of the organic matter in the at least one photo bioreactor,
   wherein the at least one photo bioreactor houses a photosynthesis organism to provide the plurality of birds with oxygen to avoid supplying oxygen from outside the poultry farm.

14. The method of claim 13 wherein consuming further comprises passing air through water in the at least one photo bioreactor at predetermined intervals.

15. The method of claim 13 wherein consuming further comprises controlling temperature of water in the at least one photo bioreactor, wherein the temperature is controlled based on a policy, wherein the policy defines a required range of temperature for each stage of a bird's life.

16. The method of claim 13 wherein consuming further comprises supplying light to the at least one photo bioreactor.

17. The method of claim 13 wherein consuming further comprises supplying exhale gases produced by the plurality of birds to the at least one photo bioreactor.

* * * * *